United States Patent
Harper et al.

[11] Patent Number: 5,877,160
[45] Date of Patent: Mar. 2, 1999

[54] COMPOSITIONS AND METHODS OF TREATMENT OF ANDROGEN-ASSOCIATED BALDNESS USING ANTISENSE OLIGOMERS

[75] Inventors: Mary Ellen Harper, Carlsbad; Tod Mitchell Woolf, Del Mar; Lyle John Arnold, Jr., Poway, all of Calif.

[73] Assignee: Genta Incorporated, San Diego, Calif.

[21] Appl. No.: 483,464

[22] Filed: Jun. 7, 1995

Related U.S. Application Data

[63] Continuation-in-part of Ser. No. 308,170, Sep. 16, 1994, abandoned, which is a continuation of Ser. No. 19,543, Feb. 19, 1993, abandoned, which is a continuation-in-part of Ser. No. 707,879, May 31, 1991, abandoned.

[51] Int. Cl.$^6$ .................................................. A61K 48/00
[52] U.S. Cl. ........................... 514/44; 435/6; 435/69.1; 436/501; 935/77; 935/78
[58] Field of Search ................................. 435/6, 69.1, 810; 436/501; 514/44, 2; 536/23.1, 24.1, 24.3, 33; 935/77, 78

[56] References Cited

U.S. PATENT DOCUMENTS 5,166,483  11/1992  Kersusan et al. ................ 200/144 A
5,556,956   9/1996  Roy et al. ........................... 536/24.1

FOREIGN PATENT DOCUMENTS 8605518  9/1986  WIPO.

OTHER PUBLICATIONS

Sanbrook et al. (1989) Molecular Cloning, vol. 2 (Cold Spring Harbor Laboratory Press, Cold Spring Harbor, NY)pp. 14.5, 14.18 and 14.19.

Tseng et al. (1994) Cancer Gene Therapy, vol. 1, No. 1, pp. 65–71.

Chang et al. (1988) Science, vol. 240, pp. 324–326.

*Primary Examiner*—Ardin H. Marschel
*Attorney, Agent, or Firm*—Knobbe, Martens, Olson & Bear, LLP

[57] ABSTRACT

Compositions and methods of treating androgen-associated hair loss, in particular decreasing the progression of male pattern baldness using a nucleoside Oligomer or Oligomers useful in the described methods are provided.

35 Claims, 4 Drawing Sheets

COMPOSITIONS AND METHODS OF TREATMENT OF ANDROGEN-ASSOCIATED BALDNESS USING ANTISENSE OLIGOMERS

CROSS-REFERENCE TO RELATED APPLICATIONS

The present application is a continuation-in-part of U.S. Ser. No. 08/308,170 filed Sep. 16, 1994, now abandoned, which is a continuation of U.S. Ser. No. 08/019,543, filed Feb. 19, 1993, now abandoned, which is a continuation in part of U.S. Ser. No. 07/707,879 filed May 31, 1991, now abandoned, the disclosures and figures of which are incorporated herein by references.

BACKGROUND AND INTRODUCTION TO THE INVENTION

Androgens are steroid hormones found circulating at varying levels in both men and women. They are essential in sex differentiation, development, and reproductive function. However, androgens can also play a role in undesirable physiological conditions, including different types of baldness.

One of the most prevalent types of baldness is male pattern baldness (MPB). This condition is widespread, affecting two of every three men. MPB, which is inherited as a autosomal dominant trait with partial penetrance, is known to be androgen-dependent. This is evidenced in the fact that castrated males do not develop baldness.

Hair follicles initially appear in utero. No new follicles are created after birth, and it is believed that none are lost in adult life. However, in MPB, hair follicles do become progressively smaller (miniaturized). Hair follicles exhibit cyclic activity. Each period of active growth of hair (anagen) alternates with a resting period (telogen), separated by a relatively short transition phase (catagen). Hair growth on the human scalp is a mosaic of follicular activity with each follicle at a stage independent of its neighbors. At any one time, between 4–24% (average 13%) of follicles are in telogen and <1% in catagen. Hairs reach a terminal or definitive length, which depends mainly on the duration of anagen, and partly on the rate of growth. In the human scalp, anagen may occupy three years or more; however, the percentage of follicles in telogen increases with age, resulting in a gradual thinning. In MPB, the ratio of telogen to anagen is increased still further. Also, in MPB the hairs in affected areas become steadily shorter and finer, and ultimately may be reduced to the short (<2 cm), fine, unpigmented hair known as vellus hair.

Although the endocrine system does not directly initiate or curtail the activity of the hair follicle, androgens do accelerate or retard the normal cyclic activity of hair growth described above.

Testosterone (T) is the major circulating androgen. Because circulating T is largely bound to sex hormone binding globulin (SHBG), the availability of T depends not only on its total concentration, but also on the level of SHBG. While plasma T levels in MPB appear to be normal, SHBG levels tend to be low. This implies that bald males may have higher levels of free testosterone. This implication is borne out by the demonstration that bald males have high T concentrations in their saliva.

T itself has minimal activity in the hair follicle. A much more active metabolite which is believed to be responsible for MPB is 5-alpha-dihydrotestosterone (DHT). DHT is formed in the cytoplasm of hair follicle cells after reduction of T by the enzyme 5-alpha-reductase. Because balding men have increased 5-alpha-reductase activity in the hair follicles and skin of the frontal scalp, it has been suggested that this enzyme may be involved in development of MPB. Two genes have been reported, each of which codes for a distinct 5-alpha-reductase enzyme (Genbank locus:HUM5AR and HUMSRDA).

The effects of androgens in MPB are mediated by the binding of an androgen (primarily DHT) to the androgen receptor (AR). Androgens bind specifically to the AR, which is either situated in the nucleus or transferred to it from the cytoplasm. The AR belongs to a subfamily of steroid/thyroid hormone/retinoic acid receptors, whose activity is controlled by the tight and specific binding of the cognate ligand. Evidence for the involvement of the AR in MPB includes the demonstration that androgenic alopecia (a type of pattern baldness in women) can be alleviated by treatment with antiandrogens. These antiandrogens, such as spironolactone, cyproterone acetate, flutamide and cimetidine, bind to the AR and competitively inhibit DHT binding. In addition, sebaceous glands of bald scalps were found to have greater binding affinity and capacity for androgens than those in hairy scalps.

In the past, baldness was treated only with surgical procedures, such as hair transplants and scalp reduction. Recently, however, there have been some advances in medical treatment of baldness. The most publicized of these is minoxidil (Rogaine™). Minoxidil is a potent vasodilator which has been used as a treatment for hypertension. A noted side effect of this treatment was the growth of hair on parts of the body. This led to the testing of topical minoxidil on balding areas of the scalp. The result in some cases was an apparent decrease in vellus hairs with a concomitant increase in terminal hairs. Many of the subjects studied reported that their rate of hair loss decreased. However, not all subjects responded to treatment with minoxidil. It was found that younger men who only recently (within five years) had begun to bald responded better than older men, and that minoxidil worked best on small areas of vertex baldness.

Research indicates that minoxidil will not help the majority of balding men, although it does help a specific population of minimally balding young men. The reason for the effectiveness of minoxidil is not known. It might be due to an increase in blood flow caused by the vasodilating effect of the drug. The longterm effects of minoxidil treatment are not known.

Other treatments are directed at reducing the production of DHT from testosterone, thereby preventing its cytosol-nuclear binding and/or translocation. Topical or intralesional progesterone can also be used to reduce the production of DHT from T. Since progesterone is similar in structure to testosterone, it competes with testosterone for 5-alpha-reductase, the enzyme that converts testosterone to DHT.

SUMMARY OF THE INVENTION

The present invention is directed to methods of treating androgen-associated hair loss, particularly hair loss in men, more particularly to methods of decreasing the progression of male pattern baldness and also to pharmaceutical compositions useful for these methods. These methods and pharmaceutical compositions are particularly suited to the treatment of hair loss associated with increased levels of protein-bound DHT in scalp. According to one aspect, Oligomers complementary to a target sequence in genes which result in increased amounts of androgen receptor bound-5-α-dihydrotesto-sterone in scalp tissue are used to down-regulate genes or their transcription products.

The topography of male pattern baldness has to do with both the number of androgen receptor ("AR") molecules of the follicular cells and the activity of 5-alpha-reductase ("5-α-RE") in different areas of the scalp. Thus, targeting 5-alpha reductase or the AR would be useful in developing a treatment for MPB. However, it is essential that the treatment act only at the scalp and is cleared quickly from the body, since systemic inhibition of testosterone or DHT activity would be highly disadvantageous in men, resulting in undesirable feminization.

The androgen receptor may be involved in other types of hair loss aside from MPB. For example, androgenic alopecia, a type of hair loss in women, has been shown to respond to treatment with antiandrogens. Accordingly, the methods and pharmaceutical compositions of the present invention may be useful in the treatment of other types of androgen-associated hair loss. Also, these methods and compositions may be useful in treating other conditions where localized (as opposed to systemic) down-regulation of the AR or 5-α-RE is desirable. Accordingly, the present invention is also directed to methods of decreasing levels of protein-bound 5-alpha-dihydrotestosterone in a localized and tissue-specific manner without significantly interfering with testosterone metabolism in other tissues or systemically by exposing the cells of the tissue to be treated with an Oligomer or Oligomers which inhibit or alter expression of the AR or 5-α-RE. Such Oligomers include those which interact with a target sequence selected from a gene coding for the AR or 5-α-RE or a sequence immediately upstream from the transcription site of the gene or their transcription products.

Thus, in one aspect, the present invention is directed to a method of treating androgen-associated hair loss by decreasing levels of 5-alpha-dihydrotestosterone which are present in follicles and bound to protein, and according to a preferred aspect decreasing levels of DHT bound to the androgen receptor in scalp tissue without significantly interfering with testosterone synthesis and/or metabolism in other tissues. This method comprises exposing scalp cells to an amount of an Oligomer or Oligomers sufficient to provide a decrease in the rate of hair loss, preferably by a cosmetically significant amount. The Oligomer or Oligomers interact with a gene coding for the AR or 5-α-RE or a sequence immediately upstream from the transcription start site of the gene or their transcription products and thereby inhibit or alter expression of the AR or 5-α-RE.

Suitable Oligomers for use in the methods and pharmaceutical compositions of the present invention include (a) an antisense Oligomer having a sequence complementary to a sequence of RNA transcribed from a target gene present in the cells; (b) an antisense Oligomer having a nucleoside sequence complementary to a single stranded DNA target sequence; (c) an antisense Oligomer having a nucleoside sequence complementary to a single RNA or DNA strand contained within a duplex (d) a Third Strand Oligomer having a sequence complementary to a selected double stranded nucleic acid sequence of a target gene present in the cells; and (e) a Triplex Oligomer Pair which is complementary to a single-stranded nucleic acid sequence of a target gene or its transcription product or to a single-stranded sequence contained within a duplex. The target gene is advantageously selected from the group consisting of those genes encoding 5-alpha-reductase and the androgen receptor. According to a preferred aspect, the oligomer is applied topically to the scalp tissue.

According to an alternate aspect, the present invention is directed to a method of treating androgen-associated hair loss which comprises exposing scalp to an amount of an Oligomer which decreases the rate of hair loss wherein said Oligomer is selected from an antisense Oligomer having a sequence complementary to that of RNA transcribed from a gene for androgen receptor or an antisense Oligomer having a sequence complementary to a sequence of RNA transcribed from a gene for 5-alpha-reductase.

According to a preferred aspect the Oligomer is a neutral Oligomer. Neutral Oligomers such as methylphosphonate oligomers are cleared rapidly through the kidneys. Especially preferred are methylphosphonate Oligomers, which are rapidly cleared from the plasma and are excreted in the urine.

The Oligomers used according to the present invention preferably comprise oligomers which have a neutral backbone. Neutral Oligomers are preferred, in part, due to their advantageous uptake through the skin when applied topically. Preferably these Oligomers are substantially neutral. More preferably, neutral oligomers are used. Particularly preferred are substantially neutral methylphosphonate Oligomers. According to an especially preferred aspect, neutral methylphosphonate Oligomers are employed.

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-5-donor/acceptor bases such as pseudoisocytosine and pseudouracil and other modified bases (such as 8-substituted purines). In RNA, the 5-carbon sugar is ribose; in DNA, it is 2'-deoxyribose. The term nucleoside also includes other analogs of such subunits, including those which have modified sugars such as 2'-O-alkyl ribose.

The term "phosphonate" refers to the group wherein R is hydrogen or an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorus group linkages (or links) to connect nucleosidyl units.

The term "Phosphodiester" or "diester" refers to the group wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of a nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage. Suitable alkyl- or aryl-phosphonate groups include alkyl- or aryl-groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the oligonucleoside or nucleoside/non-nucleoside polymer that the Oligomer conjugate comprises be substantially neutral and capable of hybridizing to its complementary target sequence.

The term "substantially neutral" in referring to an Oligomer refers to those oligomers in which at least about 80 percent of the internucleosidyl linkages between the nucleoside monomers are nonionic linkages.

The term "neutral alkyl- or aryl-phosphonate Oligomer" refers to neutral Oligomers having neutral internucleosidyl linkages which comprise at least one alkyl- or aryl-phosphonate linkage.

The term "neutral methylphosphonate oligomer" refers to neutral oligomers having internucleosidyl linkages which comprise at least one methylphosphonate linkage.

The term "tandem oligonucleotide" or "tandem Oligomer" refers to an oligonucleotide or Oligomer which is complementary to a sequence located either on the 5'- or 3'-side of a target nucleic acid sequence and which is co-hybridized with a second Oligomer which is complementary to the target sequence. Tandem Oligomers may improve hybridization of these Oligomers to the target by helping to make the target sequence more accessible to such Oligomers, such as by decreasing the secondary structure of the target nucleic acid sequence. In addition, one member of a pair of tandem Oligomers may improve the hybrid stability of the second tandem Oligomer to the target nucleic acid sequence by promoting a helical structure at either the 5'- or 3'-end of said second Oligomer and vice-versa.

The term "short chain aliphatic alcohol" refers to an alcohol having from about 2 to about 20 carbon atoms in which the aliphatic (alkyl) chain may be either straight chained or branch chained and includes primary, secondary and tertiary alcohols, glycols and polyols.

The term "flux enhancer" refers to a substance which is used to increase transdermal flux of a compound. A flux enhancer is typically applied to skin or mucous membrane in combination with the compound to increase transdermal flux of the compound. Enhancers are believed to function by disrupting the skin or mucous membrane barrier or by changing the partitioning behavior of the drug in the skin or mucous membrane.

The term "Triplex Oligomer Pair" refers to first and second Oligomers which are optionally covalently linked at one or more sites and which are complementary to and are capable of hydrogen bonding to a segment of a single stranded target nucleic acid, such as RNA or DNA, and, thus, together with the single stranded target nucleic acid, are capable of forming a triple helix structure therewith.

The term "Third Strand Oligomer" refers to Oligomers which are capable of hybridizing to a segment of a double stranded nucleic acid, such as a DNA duplex, an RNA duplex or a DNA-RNA duplex, and forming a triple helix structure therewith.

The term "complementary," when referring to a Triplex Oligomer Pair (or first and second Oligomers) or to a Third Strand Oligomer, refers to Oligomers having base sequences which are capable of forming or recognizing hydrogen bonds (and base pairing or hybridizing) with the base sequence of the nucleic acid to form a triple helix structure.

The term "substantially complementary" refers to Oligomers, including Triplex Oligomer Pairs or Third Strand Oligomers which may lack a complement for each nucleoside in the target sequence, have sufficient binding affinity for the target sequence to form a stable duplex or triple helix complex, as the case may be, and thereby specifically recognize the target sequence and selectively inhibit or down-regulate its expression.

The term "triplet" or "triad" refers to a hydrogen bonded complex of the bases of three nucleosides between a base (if single stranded) or bases (if double stranded) of a target sequence, a base of a Second Strand and a Third Strand (if a single stranded target sequence) or a base of a Third Strand (if a double-stranded target).

DETAILED DESCRIPTION OF THE INVENTION

According to the present invention, methods of arresting and/or diminishing the progression of conditions characterized by androgen-associated hair loss, particularly scalp hair loss in men, and more particularly that condition known as male pattern baldness are provided. These methods diminish and/or arrest the progression of hair loss by decreasing amounts of 5-alpha-dihydrotestosterone-androgen receptor complex present in scalp tissue. This decrease may be obtained by either down-regulation of synthesis of androgen receptor or of 5-alpha-dehydrotestosterone ("DHT"). Synthesis of DHT may be down-regulated by decreasing levels of 5-alpha reductase present in scalp tissue. Such down-regulation may be effected by use of an Oligomer which may bind to a protein's active site to modulate its function or Oligomers such as antisense Oligomers, Third Strand Oligomers and Triplex Oligomer pairs. Suitable nucleoside sequences for these Oligomers may be determined from the sequences of target genes. Preferred sequences of the target region are described herein.

A. Preferred Oligomers

The Oligomer selected may be any of a number of types, including those having a charged or uncharged backbone.

Preferred Oligomers include alkyl- and aryl-phosphonate Oligomers, especially preferred are methylphosphonate Oligomers. Other preferred Oligomers include phosphorothioate Oligomers, morpholino analogs, formacetal analogs and peptide nucleic acid ("PNA") analogs.

Preferably the Oligomers each comprise from about 4 to about 40 nucleosides, more preferably, from about 6 to 30 nucleosides. Especially preferred are Oligomers of about 8 to about 20 nucleosides.

According to an alternately preferred aspect, tandem Oligomers are employed. Preferred tandem Oligomers include those which comprise a total of about 20 to about 40 nucleosides.

Oligomers having the selected internucleoside linkages may be conveniently prepared according to synthetic techniques known to those skilled in the art. For example, commercial machines, reagents and protocols are available for the synthesis of Oligomers having phosphodiester and certain other phosphorus-containing internucleoside linkages. See also Gait, M. J., *Oligonucleotide Synthesis: A Practical Approach* (IRL Press, 1984); Cohen, Jack S., *Oligodeoxynucleotides Antisense Inhibitors of Gene Expression*, (CRC Press, Boca Raton, Fla., 1989); and *Oligonucleotides and Analogues: A Practical Approach*, (F. Eckstein, 1991). Preparation of oligomers having certain non-phosphorus-containing internucleoside linkages is described in U.S. Pat. No. 5,142,047, the disclosure of which is incorporated herein by reference.

According to an alternately preferred aspect, chirally pure Oligomers are used according to the present invention. Alternatively, Oligomers comprising at least one chirally pure internucleosidyl linkage may be used and may be preferred. Such Oligomers may be prepared using methods such as those described in Lesnikowski et al., Nucleic Acids Research 18(8):2109–2115 (1990) and Stec et al., Nucleic Acids Research 19(21):5883–5888 (1991).

Synthetic methods for preparing methylphosphonate Oligomers are described in Lee B. L., et al., *Biochemistry* 27:3197–3203 (1988), and Miller, P. S., et al., *Biochemistry* 25:5092–5097 (1986), and commonly-assigned published PCT applications WO 92/07864 and WO 92/07882 the disclosures of which are incorporated herein by reference.

Also preferred are Oligomers which are nucleoside/non-nucleoside polymers. Suitable Oligomers also include chimeric oligonucleotides which are composite RNA, DNA analogues (Inoue et al., FEBS Lett. 2115:327 (1987)). Other suitable Oligomers include Oligomers having chimeric backbones. Such chimeric backbone Oligomers include Oligomers having mixed phosphate backbones including nucleoside sequences which are capable of activating RNaseH and nucleoside sequences which do not activate RNaseH, and thus allow site directed cleavage of an RNA molecule. See U.S. Pat. No. 5,149,797 which is incorporated herein by reference. Chimeric backbone Oligomers also include Oligomers having a mixture of internucleosidyl linkages which may or may not include phosphorus atoms, such as morpholinyl linkages, formacetal linkages, peptide nucleic acid (PNA) linkages and the like. Oligomers having a neutral backbone, for example, methylphosphonate Oligomers with cleaving or cross-linking moieties attached, may prove advantageous in certain circumstances; such Oligomers may have a longer half-life in vivo since the neutral structure reduces the rate of nuclease digestion while the cleaving or cross-linking moiety may promote inactivation of target polynucleotide sequences.

According to one aspect of the present invention, these antisense Oligomers have a sequence which is complementary to a portion of the RNA transcribed from the selected target gene. Although the exact molecular mechanism of inhibition has not been conclusively determined, it has been suggested to result from formation of duplexes between the antisense Oligomer and the RNA transcribed from the target gene. The duplexes so formed may inhibit translation, processing or transport of an mRNA sequence or may lead to digestion by the enzyme RNaseH.

Single stranded Oligomers may also bind to a duplex DNA target such that a duplex is formed with one of the two DNA strands, and the second DNA of the target strand is displaced from the duplex. Preferred is the formation of a duplex by the Oligomer with the coding strand of the DNA duplex target ("invading duplex"). The invading duplex so formed may inhibit transcription.

According to an alternate aspect of the present invention, down regulation of 5-alpha reductase or the androgen receptor may be accomplished by triple helix formation using a Third Strand Oligomer or a Triplex Oligomer Pair having sequences selected such that the Oligomer(s) are complementary to and form a triple helix complex with a target sequence of double stranded or single stranded nucleic acid and thereby interfere with or prevent expression of the targeted nucleic acid sequence. Triple strand formation can occur in one of several ways. A single stranded Oligomer may form a triple strand with duplex DNA or RNA; two separate or connected Oligomers may form a triple strand with single stranded DNA or RNA; two separate or connected oligomers may bind to one of the duplex DNA or RNA strands and displace the other such that it is not involved in triple strand formation. Further descriptions of the use of Oligomers (including Third Strand Oligomers and Triplex Oligomer Pairs) to prevent or interfere with the expression of a target sequence of double or single stranded nucleic acid by formation of triple helix complexes is described in the copending U.S patent application Ser. Nos. 07/388,027, 07/751,813, 07/772,081 and 07/987,746, the disclosures of which are incorporated herein by reference.

As a general matter, the oligomer employed will have a sequence that is complementary to the sequence of the target nucleic acid. However, absolute complementarity may not be required; in general, any Oligomer having sufficient complementarity to form a stable duplex (or triple helix complex as the case may be) with the target nucleic acid is considered to be suitable. Since stable duplex formation depends on the sequence and length of the hybridizing Oligomer and the degree of complementarity between the antisense Oligomer and the target sequence, the system can tolerate less fidelity (complementarity) when longer Oligomers are used. This is also true with Oligomers which form triple helix complexes. However, Oligomers of about 8 to about 40 nucleosidyl units in length which have sufficient complementarity to form a duplex or triple helix structure having a melting temperature of greater than about 40° C. under physiological conditions are particularly suitable for use according to the methods of the present invention.

The concentration of Oligomer used may vary, depending upon a number of factors, including the extent of hair loss condition to be treated, the type and the specificity of the particular antisense Oligomer, Triplex Oligomer Pair, or Third Strand Oligomer selected. It is believed that significant inhibition as demonstrated by a cosmetically significant decrease in progression of hair loss may be obtained at concentrations in about the 10 $\mu$M range; however, under other conditions, higher or lower concentrations of Oligomer may be preferred.

Where Oligomers are to be administered transdermally, preferred are neutral oligomers.

According to one preferred aspect, these Oligomers may comprise a conjugate between a polynucleoside or nucleoside/non-nucleoside polymer and a conjugation partner. Suitable conjugation partners include intercalating agents such as acridine, alkylating agents, binding substances for cell surface receptors, lipophilic agents, photo-crosslinking agents such as psoralen, other cross-linking agents, pro-chelates, or nucleic acid modifying agents, including groups capable of cleaving a targeted portion of a nucleic acid such as hydrolytic or nucleolytic agents like o-phenanthroline copper or EDTA-iron, all of which may be incorporated in the Oligomers.

Conjugation partners may also be introduced into the Oligomer by the incorporation of modified nucleosides or nucleoside analogs through the use of enzymes or by chemical modification of the Oligomer, for example, by the use of non-nucleotide linker groups.

When used to prevent function or expression of a single or double stranded nucleic acid sequence, these Oligomers may be advantageously derivatized or modified to incorporate a nucleic acid modifying group which may be caused to react with said target nucleic acid and irreversibly modify its structure, thereby rendering it non-functional. Conjugates may be introduced to alter the pharmacodynamics or toxicity of the oligonucleotides in the body. For example, a cleavable moiety may be attached according to U.S. Pat. No. 4,588,525, such cleavable moiety being particularly useful with topical application of the conjugate. Upon application of the conjugate, that portion of conjugate that enters the blood stream instead of the tissue at the site of topical application is cleaved to a more highly charged species which only poorly enters non-target tissues and is readily excreted.

Commonly assigned U.S. Ser. No. 565,299, the disclosure of which is incorporated herein by reference, discloses psoralen-derivatized Oligomers.

As discussed above, a wide variety of nucleic acid modifying groups may be used as conjugation partners to derivatize these Oligomers. Nucleic acid modifying groups include groups which, after the derivatized Oligomer forms a complex with a single stranded or double stranded nucleic acid segment, may be caused to cross-link, alkylate, cleave, degrade, or otherwise inactivate or destroy the target nucleic acid segment or a target sequence portion thereof, and thereby irreversibly inhibit the function and/or expression of that nucleic acid segment.

The location of the nucleic acid modifying groups in the oligomer may be varied and may depend on the particular nucleic acid modifying group employed and the targeted nucleic acid segment. Accordingly, the nucleic acid modifying group may be positioned at the end of the Oligomer or intermediate between the ends. A plurality of nucleic acid modifying groups may be included.

In one preferred aspect, the nucleic acid modifying group is photoreactable (e.g., activated by a particular wavelength, or range of wavelengths of light), so as to cause reaction and, thus, cross-linking between the Oligomer and the nucleic acid target.

Exemplary of nucleic acid modifying groups which may cause cross-linking are the psoralens, such as an aminomethyltrimethyl psoralen group (AMT). The AMT is advantageously photoreactable, and thus must be activated by exposure to particular wavelength light before cross-linking is effectuated. Other cross-linking groups which may or may not be photoreactable may be used to derivatize these Oligomers.

Alternatively, the nucleic acid modifying groups may comprise an alkylating agent group which is covalently bonded to the nucleic acid segment to render the target inactive. Suitable alkylating agent groups are known in the chemical arts and include groups derived from alkyl halides, haloacetamides and the like. Polynucleotide modifying groups which may be caused to cleave the polynucleotide segment include moieties which generate radicals, as well as moieties which promote cleavage through nucleophilic attack. Transition metal chelating complexes, such as ethylenediaminetetraacetate (EDTA) or a neutral derivative thereof, can be used to generate radicals. Other groups which may be used to effect radical mediated cleavage include phenanthroline, porphyrin and the like. When EDTA is used, iron may be advantageously tethered to the Oligomer to help generate the cleaving radicals. Although iron-EDTA is a preferred polynucleotide cleaving group, other nitrogen containing materials, such as azo compounds or nitrenes or other transition metal chelating complexes, may be used. Yet other cleavage agents include nucleophilic agents and hydrolytic agents that promote the addition of water at the phosphorus internucleotide linkages. Such agents include amines, substituted guanidinium groups, imidazole groups and the like.

1. Preferred Neutral Oligomer Formulations

Preferred neutral oligomers include neutral alkyl- and aryl-phosphonate Oligomers and neutral Oligomers comprising morpholino or phosphoramidate linkages. Especially preferred are neutral methylphosphonate Oligomers. In view of their demonstrated ability to penetrate skin, including tape stripped skin, (which has had the stratum corneum removed and which has been reported as a model for mucous membrane), particularly preferred are neutral methylphosphonate Oligomers having only methylphosphonate internucleosidyl linkages.

According to another aspect of the present invention, preferred are Oligomers which may be neutral until they enter cells and once inside are converted to charged species through chemical or biological processes. Such charged oligonucleotides may contain other moieties that stabilize the oligonucleotides to nuclease degradation. Substituents such as 2'-O-methylribose groups, various base modifications, and analogs of the phosphorous backbone, such as phosphorothioates, can increase resistance to nucleases. Additionally, the presence of methylphosphonate or other neutral internucleoside linkages in the oligomer give exonuclease resistance.

Preferred are neutral Oligomers having from about 6 to about 40 nucleosides, more preferably from about 12 to about 20 nucleosides. Although neutral Oligomers which comprise more than 20 nucleosides may be used, where complementarity to a longer sequence is desired, it may be advantageous instead to employ shorter neutral tandem Oligomers which total more than 20 nucleosides in order to maximize solubility and penetration through the skin while competing for the development of a secondary structure of the target nucleic acid, such as an mRNA. These tandem oligomers may also increase specificity of binding to the target sequence. Alternatively, it may be advantageous to use a plurality of neutral Oligomers, each Oligomer complementary to a distinct target sequence which may be part of the same gene or a different gene.

Where the neutral Oligomers comprise alkyl- or aryl-phosphonate Oligomers, it may be advantageous to incorporate nucleoside monomeric units having modified ribosyl moieties. The use of nucleoside units having 2'-O-alkyl- or 2'-halo- and, in particular, 2'-O-fluoro- or 2'-O-methylribosyl moieties in these neutral Oligomers may advantageously improve hybridization of the Oligomer to its complementary target sequence.

Suitable formulations comprise about 0.0001% to about 10% by weight of neutral Oligomer.

In one preferred aspect, there are provided neutral oligomer formulations which comprise about 2% to about 100% of a short chain aliphatic alcohol. Suitable alcohols include ethanol, isopropyl alcohol, propylene glycol and glycerol. In certain studies, formulations of neutral oligomers comprising ethanol have demonstrated advantageous transdermal flux.

In an especially preferred aspect, these neutral Oligomer formulations may additionally comprise a flux enhancer. Suitable flux enhancers include those known to those skilled in the art and include decylmethylsulfoxide, dimethylsulfoxide as well as cyclic ketones, lactones, anhydrides and esters such as those described in PCT Application No. PCT/US86/02583 (Publication Number WO87/03473). Some of these flux enhancers also increase retention of the Oligomer and, thus, act to increase the concentration of Oligomer within the skin itself.

Thus, for Oligomer formulations for direct (local) treatment, such as topical application to skin, it is preferred to use a flux enhancer which not only maximizes transdermal flux, but increases Oligomer retention in the skin. Certain cyclic ketone and lactone enhancers have been reported to increase local retention as well and, thus, comprise a preferred class of enhancers for topical administration of Oligomer formulations.

According to one aspect, the present invention includes liposomal delivery of the Oligomers. Various methods and types of liposomal vesicles for drug delivery have been described. See, e.g., Remington's Pharmaceutical Sciences (1990). The Oligomers may be encapsulated by a liposome. Such liposome complexes advantageously may act to enhance delivery of Oligomer.

B. Preferred Target Genes and Target Sequences

According to a preferred aspect, the present invention is directed to methods of preventing or reducing hair loss using oligomers which interfere with the expression of the enzyme 5-alpha-reductase, or with the expression of the androgen receptor itself. Suitable Oligomers include antisense Oligomers, Third Strand Oligomers and Triplex Oligomer Pairs.

According to one aspect of the present invention, there are provided methods of decreasing hair loss by preventing or interfering with the expression of the human androgen receptor or the 5-alpha-reductase enzyme by administration of an Oligomer which is complementary to a target sequence on the DNA or an mRNA transcribed therefrom which codes for the androgen receptor or 5-alpha-reductase or to a sequence immediately upstream from the transcription start site for the mRNA. The Oligomer administered may be either an antisense Oligomer, a Third Strand Oligomer, or a Triplex Oligomer Pair. The antisense Oligomer is complementary to a sequence of RNA transcribed from a target gene, to a single-stranded DNA target sequence, or to a single RNA or DNA strand contained within a duplex. The Third Strand Oligomer has a base sequence selected so that it is capable of hydrogen bonding with a sequence of a double stranded nucleic acid and forming a triple helix complex therewith. The first and second oligomers of the Triplex Oligomer Pair have sequences selected such that they are complementary to and capable of hydrogen bonding with a targeted single-stranded nucleic acid sequence of a target gene or its transcription product or to a single strand of a duplex and together with the single stranded nucleic acid form a triple helix complex.

The target gene is selected from the group consisting of those genes encoding the androgen receptor or the enzyme 5-alpha-reductase and is considered to include a target sequence immediately upstream from the transcription start site of that gene. Preferably the target sequence would include sequences from −500 to +20 (relative to the transcription start site) of the androgen receptor gene or 5-alpha reductase gene. More perferably suitable sequences would include target sequences in the area from −100 to +20 (relative to the transcription start site) of the androgen receptor gene or 5-alpha reductase gene.

Oligomers of appropriate length, preferably from about 8 to 40 nucleosides, more preferably from about 12 to about 20 nucleosides, are selected so as to be adjacent to or cover these sites when hybridized to the target, in part or in whole. Preferred sites when the target sequence is mRNA include, in both the androgen receptor and 5-alpha-reductase genes, the 5' untranslated region, the translation initiation region including regions slightly downstream of the AUG start codon (preferably up to about 20 nucleotides downstream from the AUG initiation codon), splice acceptors, splice donors, and the 3' untranslated region.

As examples, in the case of the androgen receptor, the preferred target sites would include the sequence ranging from 13 to 50, with reference to the nucleotide positions of the human androgen receptor gene (Genbank locus:HUMARB). A preferred target of this sequence range would include the sequence:

[1] TTC CCC CAC TCT CTC TC, [SEQ. ID. NO. 1]
corresponding to the nucleotide positions 28–44 of the androgen receptor gene (Genbank locus:HUMARB). A second preferred target of this sequence range would include the sequence:

[2] CTC TCT CTC CAC CTC, [SEQ. ID. NO. 2]
corresponding to the nucleotide positions 36–50 of the androgen receptor gene. A third preferred target of this sequence range would include the sequence:

[3] 5'-GCC AAG CUC AAG GAU GGA AGU GCA G-3', [SEQ. ID. NO. 3]
corresponding to the nucleotide positions -13-12 of the androgen receptor gene. A preferred triplex target site would include the sequence range from 109–126 of exon 4 of the human androgen receptor gene (Genbank locus:HUMARC4). A preferred target of this sequence range would include the sequence:

[4] UCU CUC UUC CUU CCC, [SEQ. ID. NO. 4]
corresponding to the nucleotide positions 109–123 of exon 4 of the human androgen receptor gene.

Thus, according to a preferred aspect of the present invention, Oligomers of the appropriate length, preferably from about 8 to 40 nucleosides and more preferably from about 12 to about 25 nucleosides especially from about 12 to about 20 nucleosides, are selected so as to have sequences which hybridize sites immediately adjacent to these sites or hybridize with and cover these sites, in part or wholly, as defined by the nucleotide positions included above for 5-alpha-reductase and the androgen receptor.

When antisense Oligomers are used, the sequence of the Oligomers is the reverse complement of the sequence of the targeted region so as to be able to hybridize to the targeted region.

When Third Strand Oligomers are used, the Oligomers are selected to form sequence-specific hydrogen bonding interactions with the double stranded nucleic acid target.

When Triplex Oligomer Pairs are used, the first and second Oligomers are selected so as to form sequence specific hydrogen bonding interactions with a single stranded nucleic acid, and together form a triple helix structure.

To assist in understanding the present invention, the following examples are included which describe the results of a series of experiments. The following examples relating to this invention should not, of course, be construed in specifically limiting the invention and such variations of the invention, now known or later developed, which would be within the purview of one skilled in the art are considered to fall within the scope of the present invention as hereinafter claimed.

EXAMPLE 1

Preparation of Oligoribonucleosides

Oligoribonucleotides may be synthesized using the following procedures:

The oligoribonucleotides were synthesized using 5'-O-dimethoxytrityl-2'-O-tert-butyldimethysilyl-3'-O-N,N-diisopropyl-β-cyanoethylphosphoramidite nucleosides (purchased from either Millipore or Pennisula Laboratories). The syntheses were done on a 1 μmole scale with a Milligen 8750 automated DNA synthesizer using standard Milligen phosphoramidite procedures with the exception that the coupling times were extended to 12 minutes to allow adequate time for the more sterically hindered 2'-O-tert-butyldimethylsilyl RNA monomers to react. The syntheses were begun on control-pore glass bound 2'-O-tert-butyldimethylsilyl ribonucleosides purchased from Pennisula Laboratories. All other oligonucleotide synthesis reagents were as described in Milligen's standard protocols.

After synthesis, the oligonucleotides were handled under sterile, RNase-free conditions. Water was sterilized by overnight treatment with 0.5% diethylpyrocarbonate followed by autoclaving. All glassware was baked for at least 4 hours at 300° C.

The oligonucleotides were deprotected and cleaved from the support by first treating the support bound oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1M tetrabutylammonium fluoride in tetrahydrofuran (which contained 5% or less water) for 24 hours at room temperature. The reaction was quenched by the addition of 0.6 mL of aqueous 2M triethylammonium acetate, pH 7. Desalting of the reaction mixture was accomplished by passing the by passing the solution through a Bio-Rad 10DG column using sterile water. The desalted oligonucleotide was then dried.

Purification of the oligoribonucleotides was carried out by polyacrylamide gel electrophoresis (PAGE) containing 15% 19/1 polyacrylamide/bis-acrylamide and 7M urea using standard procedures (See Maniatis, T. et al., *Molecular Closinc: A Laboratorv Manual*, pages 184–185 (Cold Spring Harbor 1982)). The gels were 20 cm wide by 40 cm long and 6 mm in width. The oligoribonucleotides (60 OD Units) were dissolved in 200 μL of water containing 1.25% bromophenol blue and loaded onto the gel. The gels were run overnight at 300 V. The product bands were visualized by UV backshadowing and excised, and the product eluted with 0.5M sodium acetate overnight. The product was desalted with a Waters C18 Sep-Pak cartridge using the manufacturer supplied protocol. The product was then $^{32}$P labelled by kinasing and analyzed by PAGE.

EXAMPLE 2

Preparation of Phosphorothioate Oligonucleosides

Synthesis of phosphorothioate oligonucleosides on solid support was done 3' to 5' for the DNA strand. A dimethoxytrityl (DMT) protected starting nucleoside attached to solid support such as controlled pore glass was placed in a reaction vessel (300 μmoles). The DMT protecting group was removed with deblock (2.5% v/v dichloroacetic acid in dichloromethane, 30 eq.) with repeated treatment (4–7 times depending on the base) to insure complete removal of the protecting group. The support was washed with acetonitrile to remove excess acid from the support. The desired β-cyanoethyl phosphoramidite nucleoside (2 eq. with respect to starting nucleoside on support) was mixed with ethylthiotetrazole (6 eq.) with argon stirring for 5 minutes. The excess monomer and activator were washed off the support with acetontrile. The phosphite intermediate was sulfurized for 10 minutes with 3H-1,2-benzodithiole-3-one 1,1 dioxide (Beaucage reagent, 5 eq.). Cap A (40% acetic anhydride in THF) and Cap B (0.625% DMAP in pyridine) were mixed and used to cap off excess alcohols that were not coupled to the amidite monomer. The whole cycle was then repeated until the desired length oligomer was synthesized. The final DMT was removed with deblock as described above. The support was then placed in a pressure vessel and the oligomer was removed from the support and the base labile protecting groups on the heterocyclic amines removed with concentrated ammonium hydroxide. The solid support was filtered away from the ammonium hydroxide solution and the ammonia removed in vacuo. The residue was taken up in the mobile phase for the purification and the oligonucleotides purified by ion-exchange chromatography to give material that was >97% pure. The usual yields were around 1.5 mg/μmole of starting nucleoside.

EXAMPLE 3

Thermal denaturation profiles

The stabilities of triple stranded complexes formed between two MP oligomers and a complementary RNA oligomer were determined by thermal denaturation analysis. Solutions were prepared for analysis as follows: 2.4 μM MP oligomer, 1.2 μM RNA oligomer (2:1 mole ratio MP:RNA) in 10 mM potassium phosphate, 0.1M sodium chloride, 0.03% potassium sarkosylate, 0.1 mM EDTA, pH 7.2, final volume=1 mL. Each solution was heated to 80° C. and allowed to cool to 4° C. over a period of about 4 hours. The solutions were then transferred to quartz cuvettes (1 cm pathlength) and placed in a Varian Model 3E spectrophotometer equipped with a temperature control module interfaced to an IBM compatible PC computer. Temperature was varied from 5° C. to 80° C. at a rate of 1.5° C./minute and absorbance was measured continuously at 260 nm. Plots of $A_{260}$ versus temperature revealed single monophasic transitions for each of the oligomer sets described in this example.

Figure 1:
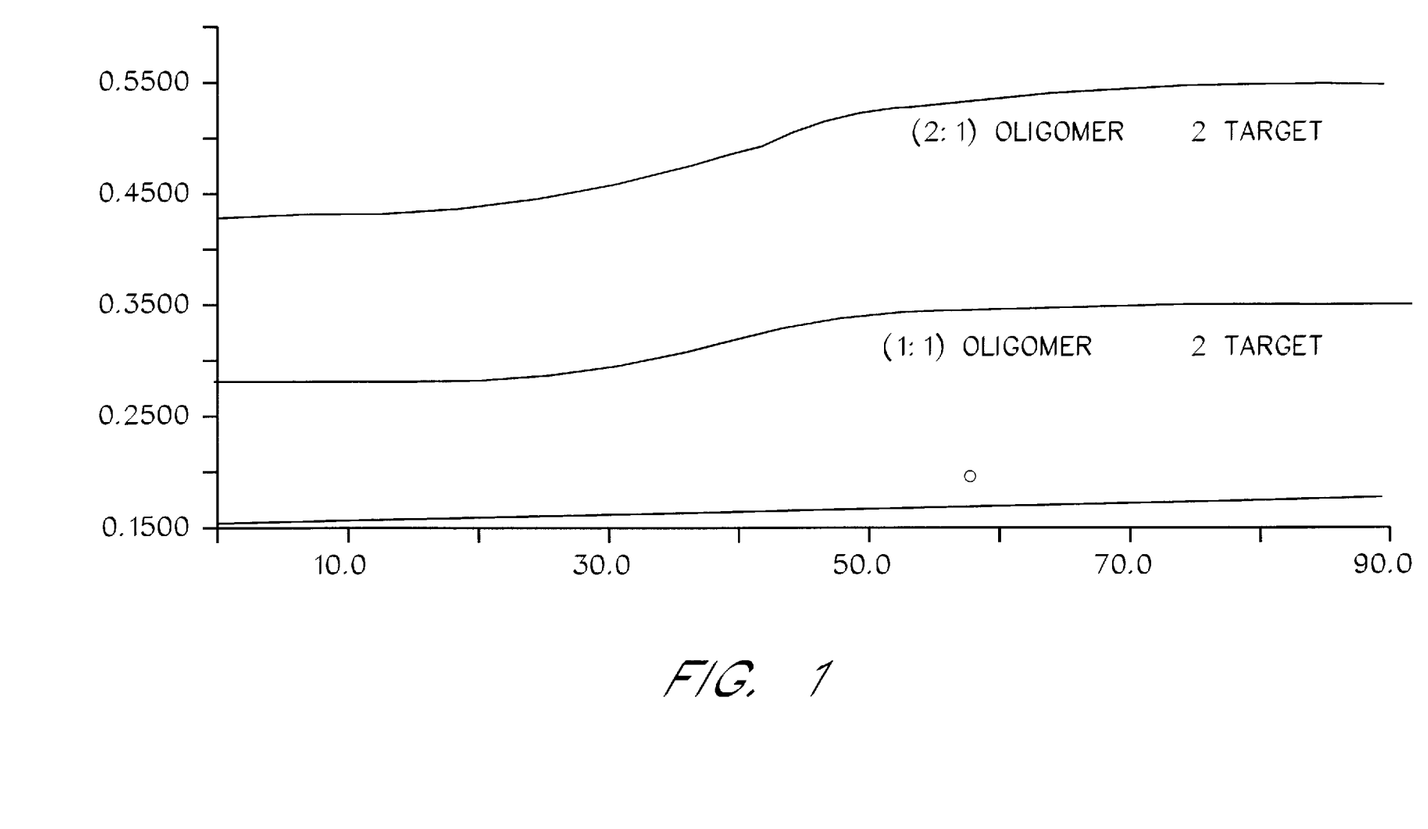
FIG. 1 depicts thermal denaturation profiles for double stranded and triple-stranded complexes formed between Oligomer 2 and a target sequence.

The melting temperatures (Tm) at which half of each complex had dissociated to single strands wa 45.8° C. and 42.3° C. (2:1 mole ration MP:RNA) for Oligomer 1 and Oligomer 2, respectively (see Table I). The entire melting curve for MP Oligomer 2 and its target at 2:1 and 1:1 ratios is shown in FIG. 1. Thus, above 2.4 micromolar MP oligomer concentration at physiological temperatures (below 37° C. in human skin) these Oligomers would be substantially hybridized.

FIG. 1 depicts a thermodenaturation profiles for double-stranded and triple-stranded complexes formed between Oligomer 2 and a target sequence.

TABLE I

| Oligomer | Tm (°C.) | (MP:RNA mole ratio) |
|---|---|---|
| [5] Oligomer 1 (Androgen Rec. #1 target: 5' gag—aga—gag—tgg—ggg—aa) [SEQ. ID. NO. 5] | 44.1° C. 45.8° C. | (1:1) (2:1) |
| [6] Oligomer 2 (Androgen Rec. #2 target: 5' gag—gtg—gag—aga—gag) [SEQ. ID. NO. 6] | 41.1° C. 42.3° C. | (1:1) (1:2) |

EXAMPLE 4

Clearance of Methylphosphonate Oligomer From Serum

Clearance of methylphosphonate oligomers from mouse serum was measured with two oligomers: $^3$H-tetramer (1689-3) $^3$H-(dT)$_4$ and a 12-mer (2054-2) $^3$H-C2-(TC)$_6$ (where C2 referred to a 2-carbon non-nucleotide linker with a primary amine).

BALB/C female mice (Jackson Laboratory) 9–10 weeks old were injected in the tail vein with 27 nmol (3×10$^5$ dpm) of oligomer in 200 μl phosphate buffered saline. Samples were collected at the indicated times by eye bleed. 100 μl samples were collected in 200 μl heparinized eye bleed capillary tubes. The mice were mildly anesthetized with metofane (methoxyflurane) during the procedure, and each mouse was bled no more than 7 or 8 times. The blood was transferred to polypropylene microcentrifuge tubes and spun to remove cells. A 20 μl aliquot of the serum was removed and combined with 5 ml of scintillation fluid (ScintiVerse BD). The amount of radioactivity was determined in a liquid scintillation counter.

Figure 2:
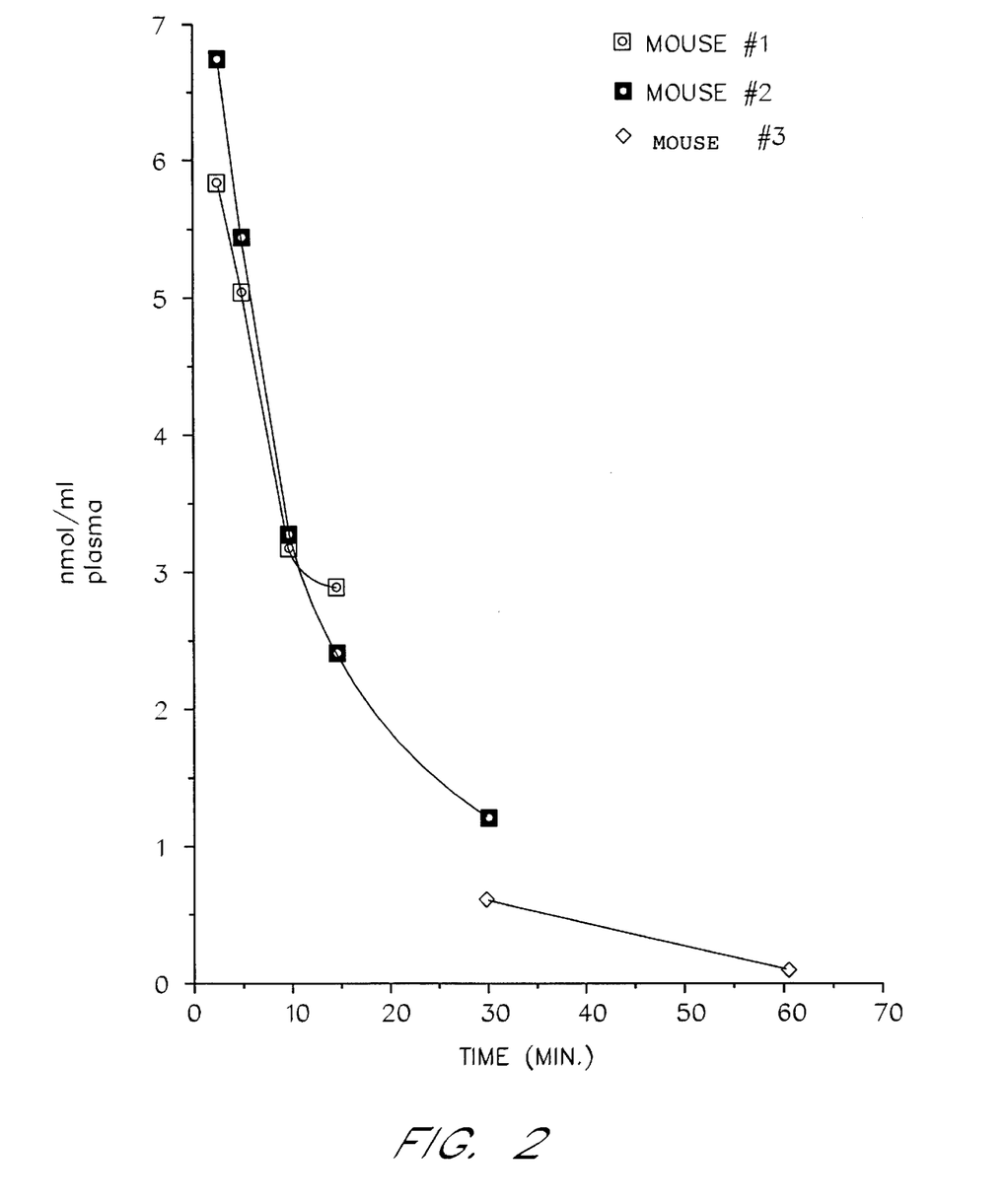
FIG. 2 depicts clearance from plasma of a tritium-labelled tetramer in a mouse model.
Figure 3:
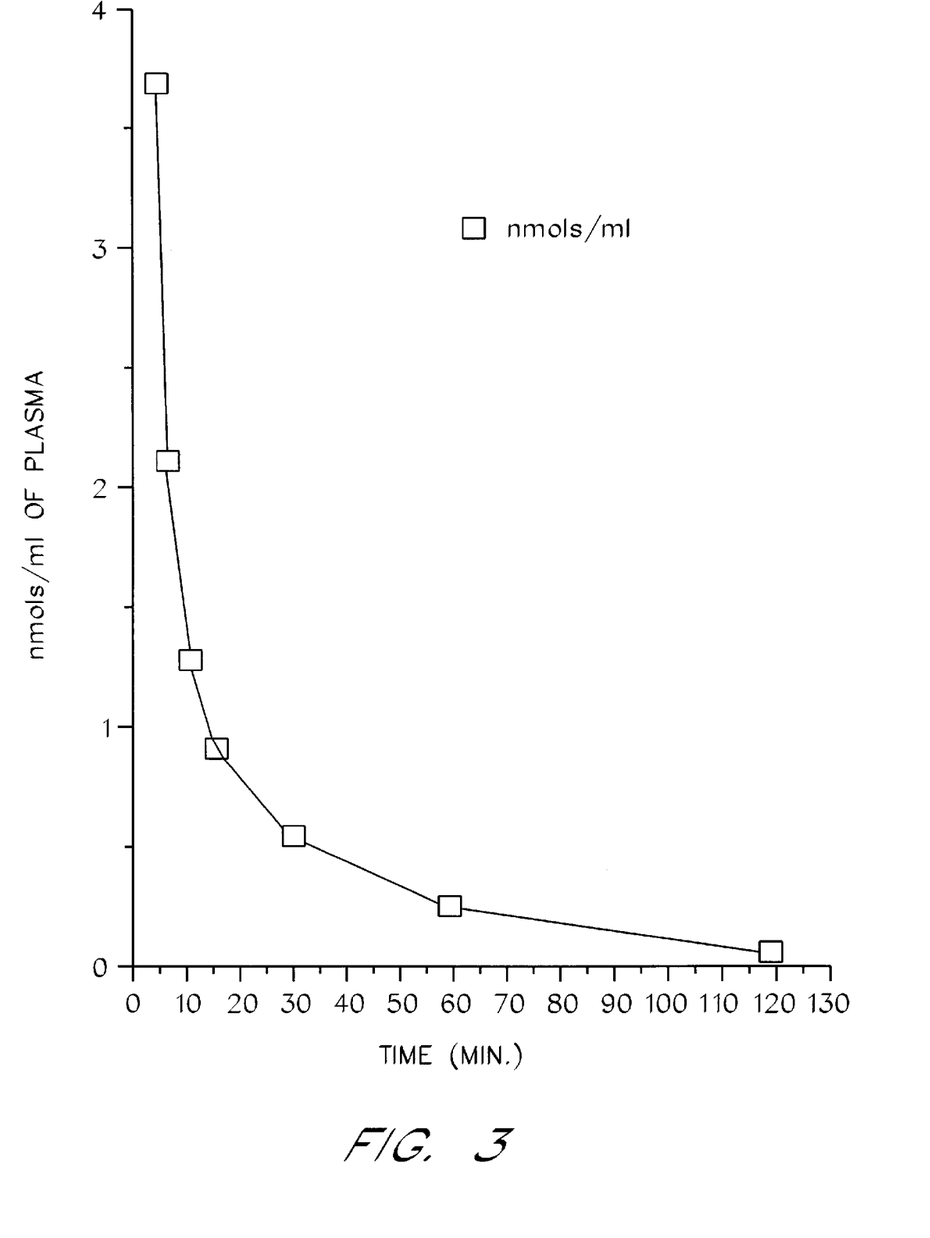
FIG. 3 depicts clearance from plasma of a tritium labelled dodecamer in a mouse model.

The plasma half-lives of both oligomers in mice were found to be approximately 8 to 10 minutes. FIGS. 2 and 3 depict plots of the clearance from plasma of the 4-mer (FIG. 2) and the 12-mer (FIG. 3).

EXAMPLE 5

Preparation of Skin Samples for Permeability and Tissue Level Studies

A. Hairless Mouse Skin

Hairless mice (male, HRS/J strain, 8 to 10 weeks old, 20 to 25 g) were sacrificed in a $CO_2$ chamber and approximately 5 cm$^2$ of full-thickness skin (dermis and epidermis) was removed from the abdomen. After removal of the subcutaneous fat, the skins were rinsed with physiological saline and used within one hour.

The stratum corneum was removed from hairless mice for permeability experiments by using cellophane tape. The tape was gently applied to the skin of a recently sacrificed animal and then pulled away from the body. This was repeated 12 to 15 times with fresh pieces of tape.

B. Human Cadaver Skin

Human cadaver skin was obtained at autopsy through the Stanford University Medical Center. The skin was excised using a dermatome from the thigh area of a 74 year old male within 24 hours post-mortem. The thickness, as measured with a Van Keuren light wave micrometer, ranged from 125 to 450 μm. The average thickness was 200 to 300 μm. The skin was rinsed with phosphate buffered saline (pH 7.4), blotted dry and frozen for 6 months in triple-sealed bags evacuated of air. Prior to use, the skin was thawed and rinsed in PBS.

EXAMPLE 6

Permeability Experiments

A diffusion console containing nine glass Franz diffusion cells was used in the permeability experiments. The Franz cells were maintained at 37° C. by thermostatically controlled water, which was circulated through a jacket surrounding the cell body. Each skin was mounted and clamped between the cell body and the cell cap so that the epidermal side faced upward (vehicle side). The skins were then allowed to equilibrate for 1 hour in the diffusion cells prior to addition of the vehicle. The exposed surface was 2.0 cm$^2$. The receptor was 0.01M phosphate-buffered saline (pH 7.4) isotonic saline with 0.05% sodium azide added to prevent growth of micro-organisms.

The Franz cells were closed to maximize drug concentration in the receptor phase. The volume of the cells was 6.2 mL. The cells were stirred using a teflon-coated stir bar at 600 rpm.

The drug/vehicle mixtures were pipetted through the cell cap onto the skin [0.2 mL total vehicle added to 2.0 cm$^2$ (0.1 nK.cm$^2$)]. At certain times following addition of the vehicles, a syringe needle was inserted through the side arm into the receptor solution and 300 μL was withdrawn. The volume removed was replaced by an equal volume of fresh saline. The solution effect was accounted for in the drug flux calculations.

Permeability results are tabulated in Table II.

EXAMPLE 7

Chromatographic Analysis of Oligomer

The 14-mer (neutral methylphosphonate Oligomer of 14 nucleosides having only methylphosphonate internucleosidyl linkages) and 14-mer-IA (methylphosphonate Oligomer of 14 nucleosides having an internal anionic internucleosidyl linkage) were measured in the receptor solution by HPLC. These analyses were performed on a Waters 840 system consisting of two model 510 pumps, a model 481 UV detector, a model 710B WISP sample processor, and a Digital computer model 350 microprocessor/programmer.

A. 14-Mer

The column used to separate the 14-mer was a 3.9 mm×15 cm 4 μm, Waters Nova-Pak C18. A gradient elution was performed as follows for the 14-mer:

| Time (min) | % A | % B |
|---|---|---|
| 0 | 100 | 0 |
| 4 | 70 | 30 |
| 10 | 55 | 45 |
| 11 | 55 | 45 |
| 12 | 5 | 95 |
| 15 | 5 | 95 |
| 17 | 100 | 0 |
| 22 | 100 | 0 |

Flow rate=1.1 mL/min, wavelength=260 nm, retention time=9.6 min.

A=0.05M TEAA, pH 7.6

B=acetonitrile/A (75:25)

B. 14-Mer-IA

The HPLC conditions were altered somewhat for measurement of the 14-mer-IA. Again, a gradient elution profile was used as described below.

| Time (min) | % A | % B |
|---|---|---|
| 0 | 0 | 100 |
| 5 | 28 | 72 |
| 14 | 45 | 55 |
| 14.2 | 45 | 55 |
| 15.5 | 98 | 2 |
| 20 | 98 | 2 |
| 22 | 0 | 100 |
| 28 | 0 | 100 |

Flow rate=1.1 mL/min, wavelength=260 nm, retention time=10.2 min.

A=Acetonitrile/B (75:25)

B=0.05M ammonium acetate, pH 7.4

EXAMPLE 8

Tissue Level Measurements of Oligomer Retained in Skin

Preliminary work was performed to determine the amount of 14-mer oligomer retained in the skin samples at the conclusion of the permeability experiments. The skins were rinsed with a small amount of water for several seconds, followed by washing for about 10 seconds with a small amount of acetonitrile to remove solid drug from the surface of the skin. The skins were then rinsed for several seconds with water. The skins were then frozen until analysis (up to several weeks). The skins were thawed and the region not exposed to the donor vehicle was cut away and discarded. The hydrated skin samples were weighed and then homogenized in 0.01M sodium phosphate, pH 7.4, using a Polytron Homogenizer for approximately 2 minutes. The homogenate was then centrifuged at 8,000 g for 15 minutes at room temperature. The supernatant was removed and analyzed directly by HPLC analysis (see below for conditions).

The chromatographic conditions were similar to those described above for the 14-mer in permeability experiments with some minor changes noted below.

| Time (min) | % A | % B |
|---|---|---|
| 0 | 100 | 0 |
| 5 | 70 | 30 |
| 14 | 55 | 45 |
| 15.5 | 2 | 98 |
| 32 | 2 | 98 |
| 35 | 100 | 0 |
| 42 | 100 | 0 |

Flow rate=1.1 mL/min, wavelength=260 nm, retention time=11.1 min.

A=0.05M ammonium acetate, pH 7.0

B=acetonitrile/A (75:25)

Presence of the oligomer in the tissue homogenates was confirmed by spiking the samples with 40 μL of a 1.8 μg/mL solution of 14-mer.

Resuspension of the pellet obtained after centrifugation, followed by homogenization and recentrifugation, led to release of between 1 to 3% of the total 14-mer recovered from the original sample. These results indicate that the 14-mer was efficiently isolated in the first extraction step.

Amounts of Oligomer isolated from skin after permeability experiments using different vehicles are tabulated in Table III.

EXAMPLE 9

Measurement of Flux and Retention of Oligomers in Human Skin

Human skin which had been dermatomed to a thickness of about 5–200 μm was used. The skin was mounted in a closed glass Franz diffusion cell (as described in Example 5).

Vehicle containing oligomer and, in some instances, enhancer (100 μL/cm²) was placed on the surface of the skin (2 cm² exposed surface).

The amount of oligomer diffusing through and remaining in the skin was measured by HPLC. (See Example 5).

Results are summarized in Table IV. Ethanol alone was found to be an effective penetration enhancer. Addition of DMS (decylmethylsulfoxide) to ethanol generally increased the penetration rate (and cumulative amount, i.e. amount penetrated over 24 hour period) of the 6-, 10- and 14-mers through human skin relative to that from ethanol alone. Addition of water to the ethanol/DMS vehicle increased the flux (and cumulative amount) still further for the 6-mer; however, flux (and cumulative amount) for the 10-mer and 14-mer was reduced.

Addition of DMS to propylene glycol increased the flux (and cumulative amount) of the 6-mer through human skin; however, the flux (and cumulative amount) was still an order of magnitude lower compared with the ethanol/DMS vehicle. Removing the stratum corneum from human skin led to a large increase in flux (and cumulative amount) of the 6-mer, although the increase was not as dramatic as that observed with hairless mouse skin.

In comparing the cumulative amount data from hairless mouse skin with human skin for the 10-mer and the 14-mer, the cumulative amount was greater in hairless mouse skin, but was generally within an order of magnitude.

Overall, an inverse relationship of permeation rate with molecular weight was observed (i.e., the higher the molecular weight, the lower the cumulative amount).

Generally, the highest retention of oligomer both in the viable tissues (dermal layer) and stratum corneum was observed from the ethanol/water/DMS vehicle. The ratio of retained oligomer in stratum corneum to dermis was about 10:30 (Note: Since there was considerably more viable tissue than stratum corneum, the majority of oligomer retained was in the dermis). Tape stripping (to remove stratum corneum) of skin did not lead to a larger amount of 6-mer being retained in dermis as compared to retention in dermis using whole skin.

Table V reports retention of 14-mer in dermis versus stratum corneum after treatment with 14-mer in various vehicle/enhancer combinations. Stratum corneum and dermis were separated before analysis by microwave treatment as described by Kumar et al. (Pharm. Res. 6:740–741 (1989)).

TABLE II

Permeability of Oligomers in Hairless Mouse (HM) and Human Skin (HS)

| Skin | Oligomer | Donor Vehicle[a] | Cumulative Amount at 24 h (μg/cm²) |
|---|---|---|---|
| HM | 14-mer | H₂O | 0.75 |
| | | EtOH | 0.28 |
| | | EtOH/DMS (95:5) | 5.5 |
| | | EtOH/DMS (97.5:25) | 4.4 |
| | | EtOH/OA (95:5)[b] | 0.30 |
| | | EtOH/OA (97.5:2.5) | 0.24 |
| | | EtAc[c] | 1.2 |
| | | EtAc/DMS (95:5) | 1.1 |
| | | EtAc4/OA (95:5) | 0.60 |
| | | EtOH[d] | 187 |
| | | EtOH/DMS (95:5)[d] | 186 |
| | | EtOH/H₂O/DMS (80:15:5) | 3.5 |
| | | EtOH/H₂O/DMS (80:15:5)[e] | 2.7 |

TABLE II-continued

Permeability of Oligomers in Hairless Mouse (HM) and Human Skin (HS)

| Skin | Oligomer | Donor Vehicle[a] | Cumulative Amount at 24 h (μg/cm²) |
|---|---|---|---|
| | | EtOH/H₂O/DMS (80:15:5)[f] | 2.1 |
| | | EtOH/H₂O/DMS (80:15:05)[g] | 0.23 |
| HM | 14-mer-IA | H₂O | 0 |
| | | EtOH | 0 |
| | | EtOH/DMS (95:5) | 0.61 |
| HS | 14-mer | EtOH | 0.26 |
| | | EtOH/DMS (95:5) | 0.24 |
| | | EtOH/OA (95:5) | 0.30 |
| | | EtOH/H₂O/DMS (80:15:5)[h] | 0.23 |

[a]Unless stated in the table footnotes, all the donor vehicles were saturated wth oligomer
[b]OA = oleic acid
[c]EtAc = ethylacetate
[d]These skins were free of stratum corneum, which was removed by tape stripping.
[e]14-mer concentration in the vehicle was 1.0 mg/mL (below saturation)
[f]14-mer concentartion in the vehicle was 0.5 mg/mL (below saturation)
[g]14-mer concentration in the vehicle was 0.05 mg/mL (below saturation)
[h]14-mer concentration in the vehicle was 1.0 mg/mL (below saturation)

TABLE III

A. Amounts of 14-mer Recovered from Skin Samples

| Skin | Donor Vehicle | μg/gm[a] | μM[b] |
|---|---|---|---|
| HM | EtOH/DMS (95:5) | 30.2 | 7.1 |
| | EtOH/DMS (95:5)[e] | 112 | 26.3 |
| | EtOH/H₂O/DMS (80:15:5) | 77 | 17.9 |
| | EtOH/H₂O/DMS (80:15:5)[d] | 18.4 | 4.3 |
| HS | EtOH/DMS (95:5) | 67.1 | 15.7 |

[a]Total μg of 14-mer recovered from the homogenized skin sample corrected for loss of 14-mer during homogenization and centriguation (see Example 6); the gm is the wet weight of the skin as measured prior to homogenization
[b]μM concentration of 14-mer in the skin were obtained from the molecular weight of the 14-mer and the assumed density of 1.0 for the skin sample (i.e., 1.0 gm of skin is equal to 1.0 cc of skin)
[c]The HM skin used in this experiment was stripped to remove the stratum corenum
[d]The concentration of 14-mer in this vehicle was 0.5 mg/mL compared to all the other experimental vehicles, which were saturated with excess solid 14-mer B. Retention of 14-mer in Whole Skin and Viable Tissue[a]

| Skin | Section | Donor Vehicle | μg/gm[b] | μM[c] |
|---|---|---|---|---|
| HM | Whole | EtOH/H₂O/DMS (80:15:5) | 63.2 | 14.8 |
| | Viable[d] | EtOH/H₂O/DMS (80:15:5) | 35.2 | 8.2 |
| HS | Whole | EtOH/H₂O/DMS (80:15:5) | 105.9 | 24.7 |
| | Viable[d] | EtOH/H₂O/DMS (80:15:5) | 7.0 | 1.6 |

[a]The weighed skin samples (hydrated) were either homogenized whole or the stratum corneum was removed, and the 14-mer xontent of the remaining tissue (viable epidermis and dermis) was determined. In each case, n = 2.
[b]Total μg of 14-mer recovered from the homogenized skin sample corrected for loss of 14-mer during homogenization and centrifugation (see Example 6); the gm is the wet weight of the skin as measured prior to homogenization
[c]μM concentration of 14-mer in the skin were obtained from the molecular weight of the 14-mer and the assumed density of 1.0 for the skin sample (i.e., 1.0 gm of skin is equal to 1.0 cc of skin)
[d]The viable tissue is the tissue after the stratum corneum has been removed by microwave treatment (Kumar, et al., Pharm. Res. 6:740–741 (1989)). It is a combination of the viable epidermis and the dermis.

TABLE IV

Penetration of Oligomers Through Skin

A. Human Skin

| Vehicle/ Enhancer | Ratio of Components | 24 Hr Cumulative Values: nmoles/cm2 Mean and SD | | |
|---|---|---|---|---|
| | | 6 Mer | 10 Mer | 14 Mer |
| EtOH/H$_2$O/ DMS | (80:15:5) | 13.8 (5.7) 2.2 (2.0) | 0.94 (1.3) | 0.18 (0.17) |
| EtOH/DMS | (95:5) | 8.2 (5.4) | 6.0 (4.2) | 0.83 (1.0) |
| EtOH | (100:0) | 3.4 (2.8) | 4.0 (6.7) | 0.37 (0.48) |
| PG | (100:0) | 0.21 (0.37) | No Data | No Data |
| PG/DMS | (95:5) | 0.57 (0.50) | No Data | No Dtat |
| EtOH/DMS (Tape Stripped) | (95:5) | 34.0 (4.8) | No Data | No Data |

The second value for the 6Mer came from a time study using a different skin donor, otherwise the data for the first three enhancers came from the same donor.
The data for the last three enhancers came from the same experiment but from a different donor.

B. Hairless Mouse

| Vehicle/ Enhancer | Ratio of Components | 24 Hr Cumulative Values: nmoles/cm2 Mean and SD | | |
|---|---|---|---|---|
| | | 6 Mer | 10 Mer | 14 Mer |
| EtOH/H$_2$O/ DMS | (80:15:5) | No Data | 2.08 (0.82) | 0.82 |
| EtOH/DMS | (95:5) | No Data | 1.94 (0.22) | 1.28 |
| EtOH | (100%) | No Data | 0.35 (0.10) | 0.065 |

EXAMPLE 10

Down-regulation of Human Androgen Receptor in Cultured Cells by Treatment with Phosphorothioate Oligonucleotides T47D cells, a breast carcinoma cell line, were seeded in 6-well plates (1.2×10$^5$/well) and 10-cm dishes (1.4×10$^6$). Cultures were grown in Minimal Essential Medium (MEM) with 10% Fetal Calf Serum. They were treated for six hours a day with antisense phosphorothioate oligonucleotide #2559 [SEQ. ID. NO. 7] (CTG CAC TTC CAT CCT TGA GCT TGG C) (See target [3], [SEQ. ID. NO. 3] at page 27) or the four-mismatch control phosphorothioate oligonucleotide #2561 (CTG CCC TTC AAT CCC TGA GTT TGG C) [SEQ. ID. NO. 8]. During the treatment cells were incubated in MEM with the oligonucleotide and 0.5–1% Lipofectin but without serum. After treatment, complete medium was restored and the cells were allowed to recover overnight. Androgen-binding capacity of the cells was assayed as described previously [Wilson, Carol M., Griffin, James E., Wilson, Jean D., Marcelli, Marco, Zoppi, Sonia, and McPhaul, Michael J. (1992) Immunoreactive Androgen Receptor Expression in Subjects with Androgen Resistance. J. Clin. Endocrinology and Metabolism 76, 1474–1478].

Figure 4:
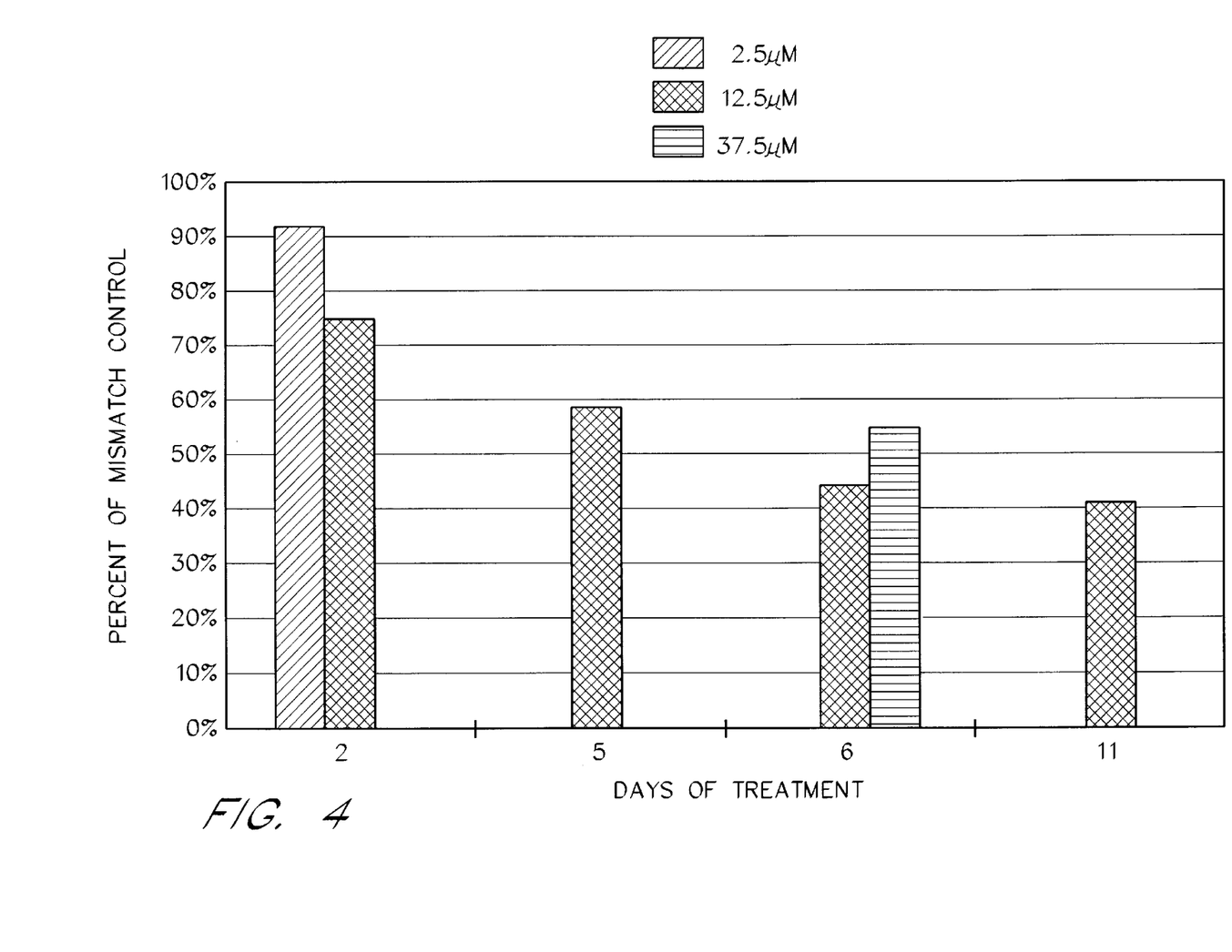
FIG. 4 depicts inhibition of DHT binding in T47D cells by an antisense phosphorothioate oligomer [SEQ. ID. NO. 7] targetted to the human androgen receptor.

The results of the androgen-binding experiments using $^3$H-dihydrotestosterone are shown in FIG. 4. After six days of treatment with 12.5 μM oligonucleotide, androgen-binding was reduced 60%. An increase to 37.5 μM did not increase the inhibitory effect. The treatment had to be carried out for at least five days to see a significant inhibition. This may reflect the relatively long half-life of the protein.

A Western Blot of extracts from the treated cells probed with rabbit polyclonal antibody raised to an amino terminal epitope of the androgen receptor confirmed the binding assay results. Androgen receptor was reduced up to 85%. In the same Western Blot assay, progesterone receptor was reduced non-specifically by 15%, but a third unrelated protein, Heat Shock Protein 70, was unaffected.

---

We claim:

1. A method of decreasing androgen-associated hair loss by decreasing levels of protein-bound 5-alpha-dihydrotestosterone present in scalp tissue without significantly interfering with testosterone metabolism in other tissues, which comprises:

exposing scalp cells to an effective amount of an Oligomer which interacts with a gene coding for androgen receptor or 5-alpha-reductase or its transcription product or a target sequence immediately upstream from the transcription start site of said gene and thereby inhibits or alters expression of the androgen receptor or 5-alpha-reductase.

2. A method according to claim 1, wherein said Oligomer specifically recognizes a target sequence, which comprises:
   (a) single stranded RNA or DNA,
   (b) double stranded DNA or RNA,
   (c) a DNA/RNA duplex, or
   (d) a single RNA or DNA strand contained within a duplex, and wherein said Oligomer interferes with transcription or translation of the target sequence.

3. A method according to claim 2, wherein the rate of hair loss is decreased at least about 10 percent.

4. A method according to claim 2, wherein said Oligomer is substantially neutral.

5. A method according to claim 4, wherein protein-bound 5-alpha-dihydrotestosterone comprises androgen receptor-bound 5-alpha-dihydrotestosterone.

6. A method according to claim 5, wherein said Oligomer comprises from about 8 to about 40 nucleosides.

7. A method according to claim 5, wherein said Oligomer comprises tandem Oligomers totaling from about 20 to about 40 nucleosides per tandem group.

8. A method of decreasing androgen-associated hair loss by decreasing levels of protein-bound 5-alpha-dihydrotestosterone in scalp tissue without significantly interfering with testosterone metabolism in other tissues, which comprises:

exposing scalp cells to an amount of an Oligomer sufficient to decrease protein-bound 5-alpha-dihydrotestosterone in said scalp cells and decrease the rate of hair loss whereby said Oligomer specifically recognizes a nucleic acid target sequence selected from the group consisting of:
   (a) single stranded RNA,
   (b) single stranded DNA,
   (c) double stranded DNA
   (d) double stranded RNA,
   (e) a DNA/RNA duplex, and
   (f) a single RNA or DNA strand contained within a duplex, whereby the Oligomer selectively interferes with transcription or translation of the nucleic acid target sequence and wherein said nucleic acid target sequence comprises a gene coding for the androgen receptor or 5-alpha-reductase or a transcription product thereof or a sequence immediately upstream from the transcription start site of the gene.

9. A method according to claim 8, wherein when said target sequence is selected from the group consisting of:
   (a) single stranded RNA:
   (b) a single DNA strand,
   (c) a single RNA strand contained within a duplex, and
   (d) a single DNA strand contained within a duplex, and wherein the Oligomer comprises an antisense Oligomer or a Triplex Oligomer Pair.

10. A method according to claim 8, wherein when said target sequence is selected from the group consisting of:
    (a) double stranded DNA
    (b) double stranded RNA, and
    (c) a DNA/RNA duplex, and wherein the Oligomer is a Third Strand Oligomer.

11. A method according to claim 8, wherein said Oligomer is substantially neutral.

12. A method according to claim 11, wherein said protein-bound 5-alpha-dihydrotestosterone comprises androgen receptor-bound 5-alpha-dihydrotestosterone.

13. A method according to claim 12, wherein said Oligomer comprises from about 8 to about 40 nucleosides.

14. A method according to claim 12, wherein said Oligomer comprises tandem Oligomers totaling from about 20 to about 40 nucleosides per tandem group.

15. A method of treating androgen-associated hair loss by decreasing levels of protein-bound 5-alpha-dihydrotestosterone present in scalp tissue without significantly interfering with testosterone metabolism in other tissues, which comprises:

exposing scalp cells to an amount of an Oligomer sufficient to decrease protein-bound 5-alpha-dihydrotestosterone in said scalp cells to produce a decrease in rate of hair loss wherein said Oligomer is selected from the group consisting of:
   (a) an antisense Oligomer having a sequence complementary to a sequence of RNA transcribed from a target gene present in the cells;
   (b) an antisense Oligomer having a nucleoside sequence complementary to a single stranded DNA target sequence;
   (c) an antisense Oligomer having a nucleoside sequence complementary to a single RNA or DNA strand contained within a duplex;
   (d) a Third Strand Oligomer having a sequence complementary to a selected double stranded nucleic acid sequence of a target sequence present in the cells; and
   (e) a Triplex Oligomer Pair which is complementary to a single stranded nucleic acid sequence of a target gene or its transcription product or to a single strand of a duplex and wherein said target gene is selected from the group consisting of those genes encoding 5-alpha-reductase and the androgen receptor or a sequence immediately upstream from the transcription start site of said gene.

16. A method according to claim 15, wherein said Oligomer is substantially neutral.

17. A method according to claim 15, whereby the rate of hair loss is decreased by at least about 10 percent.

18. A method according to claim 15, wherein said protein-bound 5-alpha-dihydrotestosterone comprises androgen receptor-bound 5-alpha-dihydrotestosterone.

19. A method according to claim 18, wherein said Oligomer is complementary to a sequence corresponding to a 5'-untranslated region, a translation initiation region, a 3'-untranslated region, a splice donor site or a splice acceptor site of a transcription product of said target gene.

20. A method according to claim 19, wherein said Oligomer is a substantially neutral Oligomer.

21. A method according to claim 20, wherein protein-bound 5-alpha-dihydrotestosterone comprises androgen receptor-bound 5-alpha-dihydrotestosterone.

22. A method according to claim 21, wherein said Oligomer or Oligomers comprise from about 8 to about 40 nucleosides.

23. A method according to claim 21, wherein said Oligomer comprises tandem Oligomers totaling from about 20 to about 40 nucleosides per tandem group.

24. A method according to claim 20, wherein said Oligomer comprises from about 12 to about 25 nucleosides.

25. A method of treating androgen-associated hair loss which comprises:
 exposing scalp to a hair loss rate diminishing amount of an Oligomer selected from the group consisting of:
  (a) an antisense Oligomer having a sequence complementary to a sequence of RNA transcribed from a gene for the androgen receptor, and
  (b) an antisense oligomer having a sequence complementary to a sequence of RNA transcribed from a gene for 5-α-reductase.

26. A method of claim 25, wherein said oligomer is a substantially neutral Oligomer.

27. A method according to claim 26, wherein said Oligomer is complementary to a member of the group consisting of: 5'-untranslated region, a translation initiation region, a 3'-untranslated region, a splice donor site, and a splice acceptor site of said RNA.

28. A method according to claim 27, wherein said Oligomer comprises from about 12 to about 25 nucleosides.

29. A method of decreasing levels of protein-bound 5-alpha-dihydrotestosterone in a selected tissue without significantly interfering with testosterone metabolism in other tissues or systemically, which comprises:
 exposing cells of the selected tissue with an effective amount of an Oligomer which interacts with a gene coding for androgen receptor or 5-alpha-reductase or its transcription product or a target sequence immediately upstream from the transcription start site of said gene and thereby inhibits or alters expression of the androgen receptor or 5-alpha reductase.

30. A method according to claim 29, wherein said Oligomer or Oligomers specifically recognize a target sequence selected from the group consisting of:
 (a) single stranded RNA,
 (b) single stranded DNA,
 (c) double stranded DNA,
 (d) double stranded RNA,
 (d) a DNA/RNA duplex,
 (e) a single RNA strand contained within a duplex, and
 (f) a single DNA strand contained within a duplex, and wherein said Oligomer interferes with transcription or translation of the target sequence.

31. A method according to claim 30, wherein the rate of hair loss is decreased at least about 10 percent.

32. A method according to claim 30, wherein said Oligomer is substantially neutral.

33. A method according to claim 32, wherein protein-bound 5-alpha-dihydrotestosterone comprises androgen receptor-bound 5-alpha-dihydrotestosterone.

34. A method according to claim 33, wherein said Oligomer comprises from about 8 to about 40 nucleosides.

35. A method according to claim 33, wherein said Oligomer comprises tandem Oligomers totaling from about 20 to about 40 nucleosides per tandem group.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

T T C C C C C A C T     C T C T C T C     1 7

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTCTCTCTCC ACCTC                                                                           15

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

GCCAAGCUCA AGGAUGGAAG UGCAG                                                                25

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

UCUCUCUUCC UUCCC                                                                           15

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

GAGAGAGAGT GGGGGAA                                                                         17

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

GAGGTGGAGA GAGAG                                                                           15

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

CTGCACTTCC ATCCTTGAGC TTGGC                                                                25

( 2 ) INFORMATION FOR SEQ ID NO:8:

( i ) SEQUENCE CHARACTERISTICS:
        ( A ) LENGTH: 25 base pairs (B) TYPE: nucleic acid
(C) STRANDEDNESS: single
(D) TOPOLOGY: linear (x i) SEQUENCE DESCRIPTION: SEQ ID NO:8:

CTGCCCTTCA ATCCCTGAGT TTGGC                                                                                          2 5